(12) United States Patent
Mori et al.

(10) Patent No.: US 7,753,899 B2
(45) Date of Patent: Jul. 13, 2010

(54) DISPOSABLE ABSORBENT ARTICLE

(75) Inventors: Kazuyo Mori, Tsurugi-cho (JP); Kenji Nakaoka, Tsurugi-cho (JP); Masaru Fujioka, Tsurugi-cho (JP); Taichiro Suzuki, Tsurugi-cho (JP); Sayaka Sato, Aizumi-cho (JP)

(73) Assignee: Livedo Corporation, Ehime (JP)

( * ) Notice: Subject to any disclaimer, the term of this patent is extended or adjusted under 35 U.S.C. 154(b) by 0 days.

(21) Appl. No.: 10/557,960

(22) PCT Filed: Jun. 20, 2003

(86) PCT No.: PCT/JP03/07845

§ 371 (c)(1),
(2), (4) Date: Nov. 22, 2005

(87) PCT Pub. No.: WO2004/112672

PCT Pub. Date: Dec. 29, 2004

(65) Prior Publication Data

US 2006/0206090 A1 Sep. 14, 2006

(51) Int. Cl.
*A61F 13/15* (2006.01)

(52) U.S. Cl. ............. 604/385.28; 604/365; 604/385.27; 604/385.01; 604/385.04; 604/367; 156/229

(58) Field of Classification Search ................. 604/365, 604/385, 28, 385.27, 385.01, 385.04, 367; 156/229

See application file for complete search history.

(56) References Cited

U.S. PATENT DOCUMENTS 3,626,899 A * 12/1971 Spellman ..................... 119/169
4,904,251 A * 2/1990 Igaue et al. ............. 604/385.26
5,188,627 A 2/1993 Igaue et al.
5,415,644 A 5/1995 Enloe (Continued)

FOREIGN PATENT DOCUMENTS

EP 0 446 867 9/1991

(Continued)

*Primary Examiner*—Tatyana Zalukaeva
*Assistant Examiner*—Ilya Y Treyger
(74) *Attorney, Agent, or Firm*—Jordan and Hamburg LLP (57) ABSTRACT

In a rising gathered member 4 of an absorbent main body 3 attached to an external sheet 2, an inward folded base end 4*b* is joined astride a side end 13*a* of a top sheet 13 as a top surface of the absorbent main body 3 and a side end 14*a* of a back sheet 14 so that the rising gathered member 4 rises from a most side edge 3*a* in a width direction of the absorbent main body 3 and, also, the back sheet 14 of the absorbent main body 3 is attached onto a skin-contacting surface side of a crotch part R of a second external sheet 8 at an inward position at a prescribed width W5 from the most side edge 3*a* of the absorbent main body 3 as an outermost joint position. With the above constitution, it is possible to effectively prevent any lateral leakage of urine and the like, even if a disposable absorbent article is shifted. Moreover, the base end of the rising gathered member is merely joined to the side end of the top surface of the absorbent main body, thereby requiring no sheet winding step or the like, such a simple process can achieve inexpensive production, and further, the stability of product precision becomes improved.

14 Claims, 6 Drawing Sheets

U.S. PATENT DOCUMENTS

| | | | |
|---|---|---|---|
| 5,476,458 A | | 12/1995 | Glaug et al. |
| 5,582,606 A | | 12/1996 | Bruemmer et al. |
| 5,584,828 A | * | 12/1996 | Yamamoto et al. ..... 604/385.28 |
| 6,045,545 A | | 4/2000 | Vandemoortele et al. |
| 6,312,420 B1 | * | 11/2001 | Sasaki et al. ........... 604/385.28 |
| 6,423,042 B1 | | 7/2002 | Sasaki |
| 6,436,081 B1 | * | 8/2002 | Wada et al. ............ 604/385.01 |
| 6,569,140 B1 | * | 5/2003 | Mizutani et al. ....... 604/385.28 |
| 6,635,798 B1 | * | 10/2003 | Yoshioka et al. ............ 604/365 |
| 2001/0056268 A1 | * | 12/2001 | Mizutani et al. ............ 604/365 |

FOREIGN PATENT DOCUMENTS

| | | |
|---|---|---|
| EP | 0 600 494 | 6/1994 |
| EP | 0 678 289 | 10/1995 |
| EP | 0 953 325 | 11/1999 |
| EP | 1 219 274 | 7/2002 |
| GB | 2 253 131 | 2/1992 |
| JP | 2-58427 | 4/1990 |
| JP | 4-9153 | 1/1992 |
| JP | 2 253 131 | 2/1992 |
| JP | 5-76565 | 3/1993 |
| JP | 7-289583 | 11/1995 |
| JP | 8-209403 | 8/1996 |
| JP | 9-154881 | 6/1997 |
| JP | 9-507768 | 8/1997 |
| JP | 10-500590 | 1/1998 |
| JP | 3047219 | 1/1998 |
| JP | 11-299828 | 11/1999 |
| JP | 11-347065 | 12/1999 |
| JP | 2000-296149 | 10/2000 |
| JP | 2001-276120 | 10/2001 |
| WO | WO-95/15140 | 6/1995 |
| WO | WO-95/31952 | 11/1995 |
| WO | WO-98/08474 | 3/1998 |

* cited by examiner

DISPOSABLE ABSORBENT ARTICLE

TECHNICAL FIELD

The present invention relates to a disposable absorbent article capable of absorbing urine and the like.

BACKGROUND ART

Figure 7:
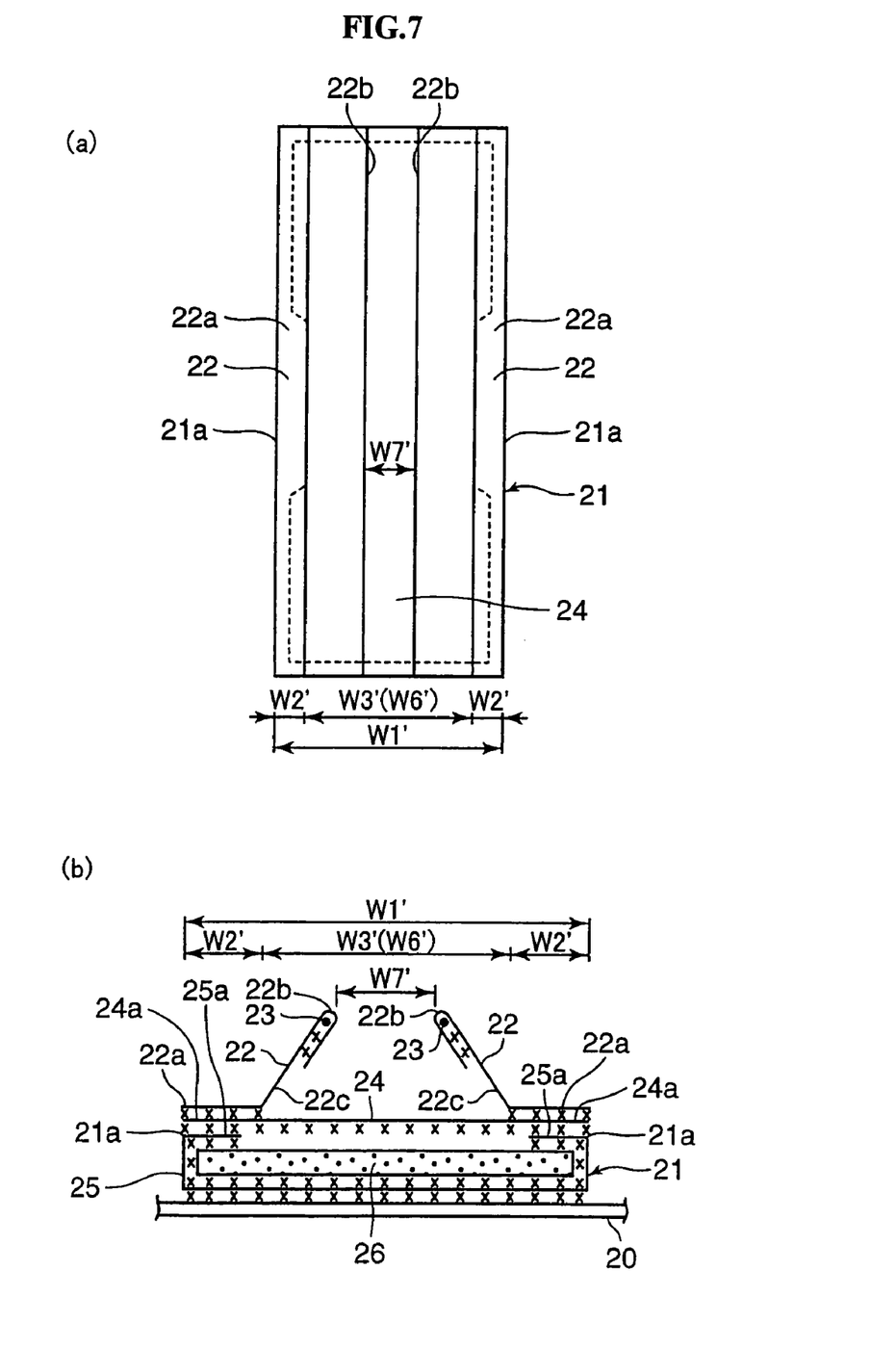
FIGS. 7(a) and 7(b) are a plan view showing a conventional absorbent main body and a schematically enlarged cross-sectional view taken along the line A-A of FIG. 2, respectively.

There has been proposed a disposable absorbent article such as a disposable diaper of the pants type, in which there is provided an exterior sheet of the pants type including a waist opening formed at the upper portions of a front section and a back section and leg openings formed on both sides of a crotch part between the front section and the back section, and further, there are provided an absorbent main body 21 joined onto a skin-contacting surface side of an exterior sheet 20 of the pants type and rising gathered members 22 having base ends 22a joined to both side ends of the absorbent main body 21, respectively, and lengthwise extending elastic members 23 joined to free ends 22b in an elongated state, respectively, as shown in FIGS. 7(a) and 7(b).

In the absorbent main body 21, an absorbent material 26 is interposed between a liquid-permeable top sheet 24 and a liquid-impermeable back sheet 25. The back sheet 25 is joined (see marks x) to the absorbent material 26 in such a state that both side ends 25a are folded inward at the upper surface of the absorbent material 26. The top sheet 24 is joined (see marks x) at both side ends 24a thereof astride the upper surface of the absorbent material 26 and the respective upper surfaces of both side ends 25a of the back sheet 25. The base ends 22a of the rising gathered members 22 are bent outward, to be joined (see marks x) to the respective upper surfaces of both side ends 24a of the top sheet 24.

The absorbent main body 21 is attached by joining (see marks x) the entire lower surface of the back sheet 25 onto the skin-contacting surface side of the exterior sheet 20.

However, the base ends 22a of the rising gathered members 22 are bent outward, to be thus joined to the respective upper surfaces of both side ends 24a of the top sheet 24, so that rising portions 22c of the rising gathered members 22 are not raised from both most side ends 21a in a width direction of the absorbent main body 21 but raised from positions inward by a width W2' of the base ends 22a.

Therefore, since the surface of the absorbent main body 21 is covered with the base ends 22a by a width W2'+W2', an absorption effective width W3' with respect to the entire width W1' of the absorbent main body 21 (i.e., a rising width W6' between the right and left rising gathered members 22) is reduced, thereby reducing an effective contact area with the skin. Similarly, since a spatial width W7' between the rising gathered members 22 also becomes small, the rising gathered member 22 is liable to fall down on the absorbent main body 21, thereby also reducing an effective contact area between the skin and the absorbent main body 21.

If this causes a diaper to be shifted, there possibly arises a problem that urine and the like are liable to laterally leak.

In addition, in the case where the disposable absorbent article is used in an overlap of a replaceable urine pad on the absorbent main body 21, the wide urine pad cannot be laid in an overlap if the width W6' between the rising gathered members 22 is small, and further, the rising gathered members 22 fall outward if the urine pad is forcibly laid in an overlap, thereby raising a problem that urine and the like are liable to laterally leak.

In view of the above problems, there has been proposed a technique of increasing the width W6' between the rising gathered members 22 (see JP-A 2001-276120). However, a top sheet winding-up step and the like are required, and therefore, a production process becomes complicated, thereby raising problems that the price of products is increased and the precision of products is poor.

The present invention has been completed to solve the above problems, and therefore, an object of the present invention is to provide a disposable absorbent article, which can be produced at a low cost in a simple process and can effectively prevent any lateral leakage of urine and the like.

DISCLOSURE OF THE INVENTION

The present invention provides a disposable absorbent article comprising an absorbent main body in which an absorbent material is interposed between a liquid-permeable top sheet and a liquid-impermeable back sheet; and rising gathered members disposed at both side ends of a top surface of the absorbent main body, wherein the rising gathered member includes a lengthwise extending elastic member joined to a free end in an elongated state and an inward folded base end joined to the side end of the top surface in such a manner that a rising portion raises from a most side edge in a width direction of the absorbent main body.

BEST MODE FOR CARRYING OUT THE INVENTION

The embodiments of the present invention will be described below in detail by reference to the drawings.

Figure 1:
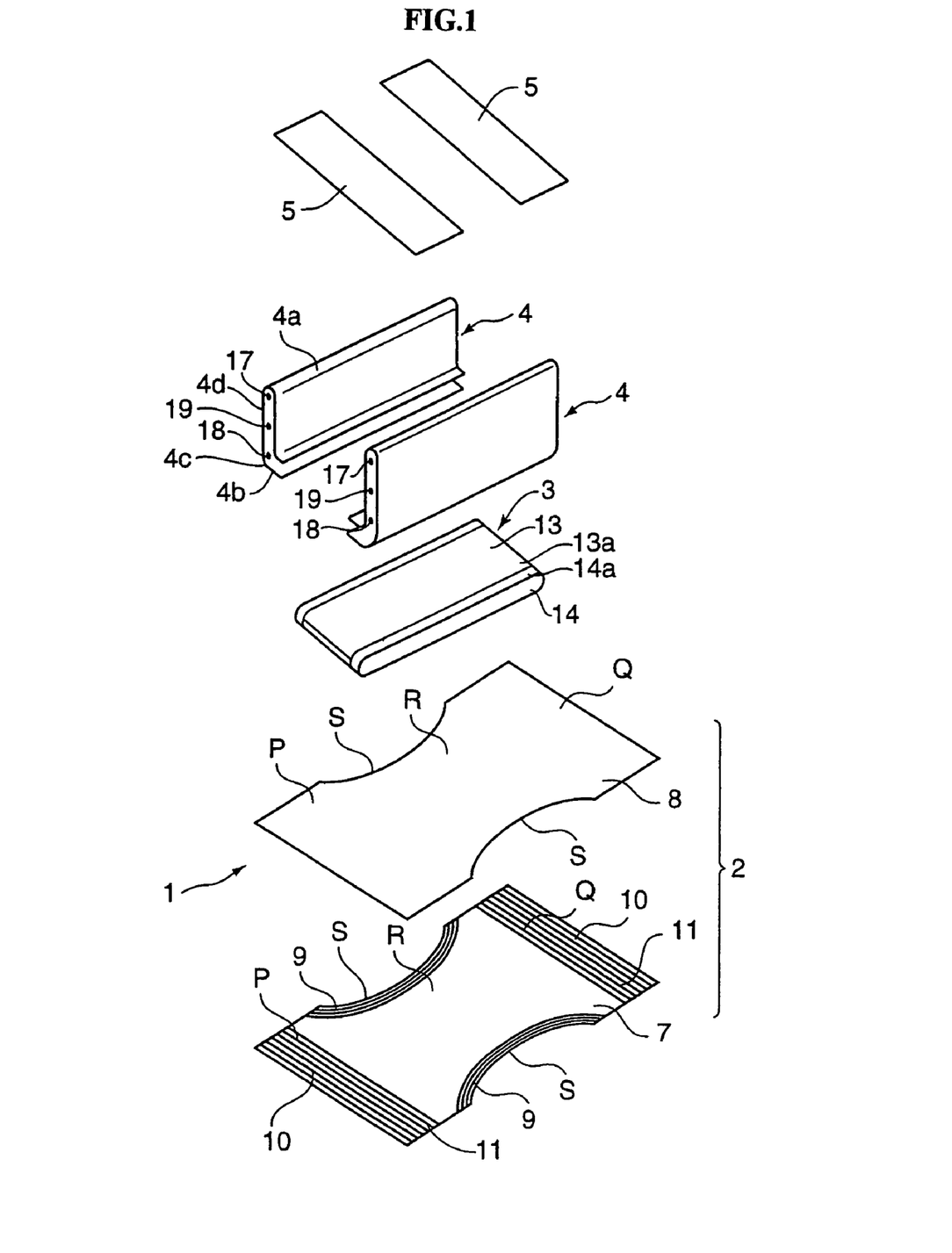
FIG. 1 is an exploded perspective view showing a disposable diaper of the pants type.

A disposable diaper 1 of the pants type is composed basically of an external sheet 2, an absorbent main body 3, right and left rising gathered members 4, and front and back waist guards 5.

The external sheet 2 includes a first external (outer surface) sheet 7, a second external (skin-contacting surface) sheet 8, elastic yarns 9 for legs, elastic yarns 10 for a waist, and elastic yarns 11 for body fitting.

The first external sheet 7 and the second external sheet 8 are formed in the contour of the disposable diaper 1 of the pants type, and further, leg openings S are formed on both sides of a crotch part R between a front section P and a back section Q.

Each of the external sheets 7 and 8 may preferably be made of a synthetic fiber non-woven fabric having excellent air permeability. At the upper surface of the first external sheet 7, the leg elastic yarn 9 is joined in a semi-circular shape along an opening edge of each of the leg openings S in an elongated state so as to form an elastic portion for a leg, and further, the waist elastic yarn 10 is joined straight in a lateral direction along the outer edge of each of the front section P and the back section Q in an elongated state so as to form an elastic portion for a waist. Moreover, on each of the front section P and the back section Q, the body fitting elastic yarn 11 is joined straight in the lateral direction in an elongated state so as to form an elastic portion for body fitting. The joining may preferably be achieved by bonding with a hot-melt adhesive, which holds true in the same manner in the following.

The second external sheet 8 is bonded onto the upper surface of the first external sheet 7 in such a state that the elastic yarns 9 to 11 are interposed therebetween, thereby forming the external sheet 2.

The external sheet 2 need not be made of a liquid-impermeable material having no air permeability, for example, a synthetic resin film material, since the disposable absorbent article in the present embodiment is formed such that the absorbent main body 3 basically inhibits urine and the like. Although the external sheet 2 may have a single-layered structure consisting of one sheet, it may preferably have a double-layered structure since the elastic yarns 9 to 11 need be bonded thereto, and further, it may have a structure consisting of three or more layers. Moreover, the external sheet 2 should have some tensile strength and is required to be inexpensive. In view of this, a span-bond non-woven fabric is preferred. However, the external sheet 2 is not limited thereto, but may be made of an ordinary non-woven fabric or a composite sheet obtained by inserting another non-woven fabric such as a melt-blown non-woven fabric between single- or double-layered non-woven fabrics to add a function. Furthermore, a non-woven fabric obtained by highly blending natural fibers or regenerated fibers may be used in combination in order to achieve a pleasant touch to a synthetic fiber non-woven fabric.

Examples of the non-woven fabric materials include polyolefin fibers made of polypropylene, polyethylene, or the like; polyester fibers made of polyethylene terephthalate or the like; synthetic fibers such as polyamide fibers made of nylon or the like; cellulose type fibers such as rayon, cotton, regenerated fibers, pulp fibers, and the like. In these fibers, span-bond non-woven fabrics made of polypropylene or polyester type span-bond non-woven fabrics may preferably be used in comprehensive consideration of water repellency, strength, costs, and the like. There may also be used SMS (i.e., a triple-layered type non-woven fabric consisting of a span-bond non-woven fabric, a melt-blown non-woven fabric, and a span-bond non-woven fabric), SMMS, and the like.

Each of the elastic yarns 9 to 11 may be made of polyurethane, natural rubber, foamed urethane, or the like, wherein the yarn may be used alone or a plurality of the yarns may be joined to each other. In addition, the yarn is not limited to a yarn shape, but may be used in a ribbon- or film-like shape.

The absorbent main body 3 is composed of a liquid-permeable top sheet 13, a liquid-impermeable back sheet 14, and an absorbent material 15. The absorbent material 15 is shown as an absorbent material formed into a hourglass shape, but it may be formed into a rectangular shape or the like.

Although the top sheet 13 is made of, for example, a liquid-permeable non-woven or woven fabric formed of a thermoplastic synthetic fiber such as polyester or polypropylene, a natural fiber or a regenerated fiber, the non-woven or woven fabric is not limited to a non-woven or woven fabric formed of such a single fiber as described above, but may be formed of the above fibers in combination.

Moreover, since the liquid permeability, which is to rapidly permeate liquid, is required for the top sheet 13, and further, since the top sheet 13 is used in direct contact with the surface of wearer' skin, a pleasant touch is required. Therefore, at least the center region of the top sheet 13 may preferably be made of a hydrophilic fiber. In order to prevent urine and the like absorbed by the absorbent material 15 from exuding outside, the regions at both ends in a vertical direction or the regions at both ends in a lateral (width) direction may be made water repellent or may be made of a water repellent fiber material.

The back sheet 14 is formed of a liquid-impermeable film made of polyethylene or the like, or a non-woven or woven fabric having a leakage preventing property. In the case where the liquid-impermeable film is used, a well-known moisture-permeable film may preferably be used to prevent any moisture.

The absorbent material 15 is made mainly of previously well-known cotton-like pulp, which is obtained by uniformly mixing a superabsorbent polymer into a cotton-like pulp fiber layer, followed by blending a thermoplastic short fiber in some case, or which may be of the non-pulp type, obtained by sandwiching a superabsorbent polymer between layers consisting of rayon non-woven fabrics or the like. In the latter case, it is favorable that since the absorbent material 15 is a remarkably thin sheet, any bulkiness of the disposable diaper 1 of the pants type can be prevented, and further, the disposable diaper 1 of the pants type can be formed almost as underwear.

As the above superabsorbent polymer, there is used those of the starch-type polymer, the cellulose-type polymer, or the synthetic polymer-type. Specific examples of the superabsorbent polymer include saponified materials of a starch-acrylate (salt) graft polymer or a starch-ethyl acrylate graft copolymer; saponified materials of a starch-methyl methacrylate graft copolymer; saponified materials of a starch-acrylonitrile graft copolymer; saponified materials of a starch-acrylamide graft copolymer; acrylate (salt) polymers; polyacrylate cross-linked polyethylene oxide; sodium carboxymethylcellulose cross-linked materials; and cross-linked materials of a polyvinyl alcohol-maleic anhydride reactant.

As the above cotton-like pulp, there is used a pulp having a fiber length of 5 mm or smaller, obtained by splitting a chemical pulp sheet, a used paper pulp sheet, or a mechanical pulp sheet with a grinder. Examples of the pulp raw material include broad-leaved trees, straw, bamboo, and kenaf in addition to needle-leaved trees.

The absorbent main body 3 is basically formed by interposing the absorbent material 15 between the top sheet 13 and the back sheet 14. A diffusion layer (i.e., a second sheet) may be provided between the top sheet 13 and the absorbent material 15, for allowing urine and the like to be uniformly and rapidly absorbed by the absorbent material 15 while being diffused. The diffusion layer is made of a non-woven fabric, a woven fabric, a porous plastic, a cotton-like pulp, or the like, having liquid permeability, which is made of a material such as polypropylene, polyethylene, polyester, rayon, pulp, or a composite fiber thereof.

Figure 4:
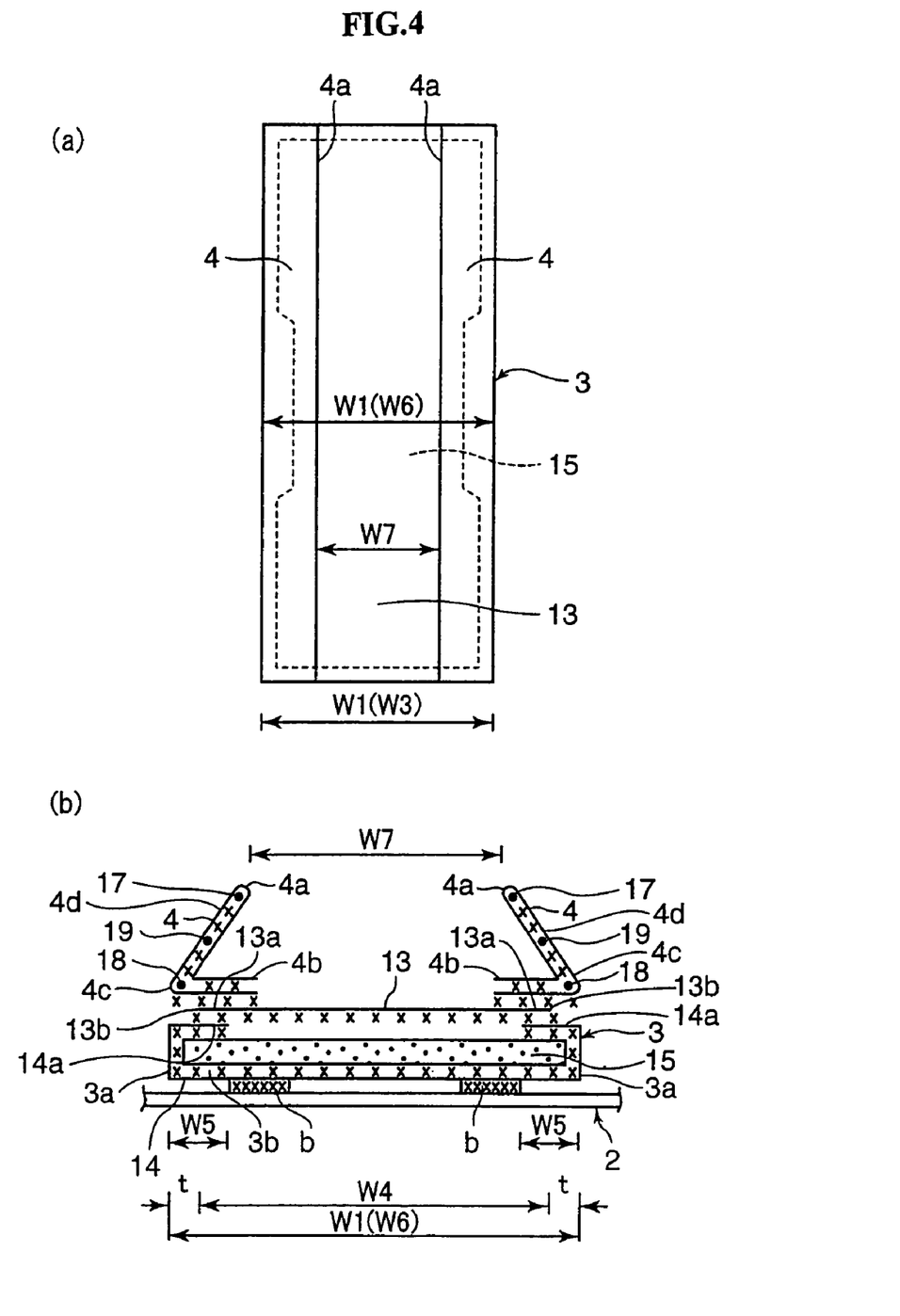
FIGS. 4(a) and 4(b) are a plan view showing an absorbent main body and a schematically enlarged cross-sectional view taken along a line A-A of FIG. 2, respectively.

As specifically shown in FIGS. 4(a) and 4(b), in the absorbent main body 3, the back sheet 14 is bonded (see marks x) to the absorbent material 15 in such a state that the back sheet 14 covers the lower and side surfaces of the absorbent material 15 and both side ends 14a are folded inward at the upper surface of the absorbent material 15.

Moreover, the top sheet 13 is set to have a width W4 smaller than the entire width W1 of the absorbent main body 3, and therefore, is joined (see marks x) astride the upper surface of the absorbent material 15 and the upper surfaces of the side ends 14a of the back sheet 14. The top sheet 13 may preferably be joined by a curtain spray system or a spiral spray system with a hot melt adhesive, thereby preventing any deterioration of liquid permeability.

A clearance "t" is to be formed between each of the respective end edges 13b of both side ends 13a of the top sheet 13 and each of both most side edges 3a of the absorbent main body 3 by setting the width W4 of the top sheet 13 to be smaller than the entire width W1 of the absorbent main body 3.

Each of the right and left rising gathered members 4 is set to have substantially the same length as that of the absorbent main body 3, and further, the gathered member 4 is folded in two and joined (see marks x) over the entire width. A first gathering elastic yarn 17 is joined to a free end (i.e., an upper folded portion) 4a of each of the rising gathered members 4 in a lengthwise elongated state, thus naturally raising each of the folded portions 4a.

In addition, a second gathering elastic yarn 18 is joined to a rising base portion 4c of each of the rising gathered members 4 in a lengthwise elongated state, and further, a third gathering elastic yarn 19 is joined to a rising portion 4d between the second gathering elastic yarn 18 and the first gathering elastic yarn 17 in a lengthwise elongated state.

Each of the gathering elastic yarns 17 to 19 is made of a polyurethane yarn or the like in the same manner as the above elastic yarns 9 to 11, wherein the yarn may be used alone or a plurality of the yarns may also be joined to each other.

In each of the rising gathered members 4, a base end 4b is folded inward in a state separated in the width direction of the absorbent main body 3, and then, is joined (see marks x) astride each of both side ends 13a of the top sheet 13 and each of both side ends 14a of the back sheet 14 in such a manner that the rising portion 4d rises from the most side edge 3a in the width direction of the absorbent main body 3. Consequently, the base end 4b of each of the rising gathered members 4 can seal the end edge 13b of each of the side ends 13a of the top sheet 13 with a width of the clearance "t", as shown in detail in FIG. 5(a).

A rising height of each of the rising gathered members 4 may preferably be in the range of 15 mm to 30 mm, and more preferably, 20 mm to 25 mm. If the rising height is smaller than 15 mm, the rising gathered member 4 is too low as a leakage preventing wall. In contrast, if the rising height is greater than 30 mm, the clearance of the gathering width becomes undesirably small.

In view of this, the absorbent main body 3 with the rising gathers is formed such that the absorbent main body 3 is attached by joining the back sheet 14 onto the skin-contacting surface side of the second external sheet 8 of the external sheet 2.

Figure 2:
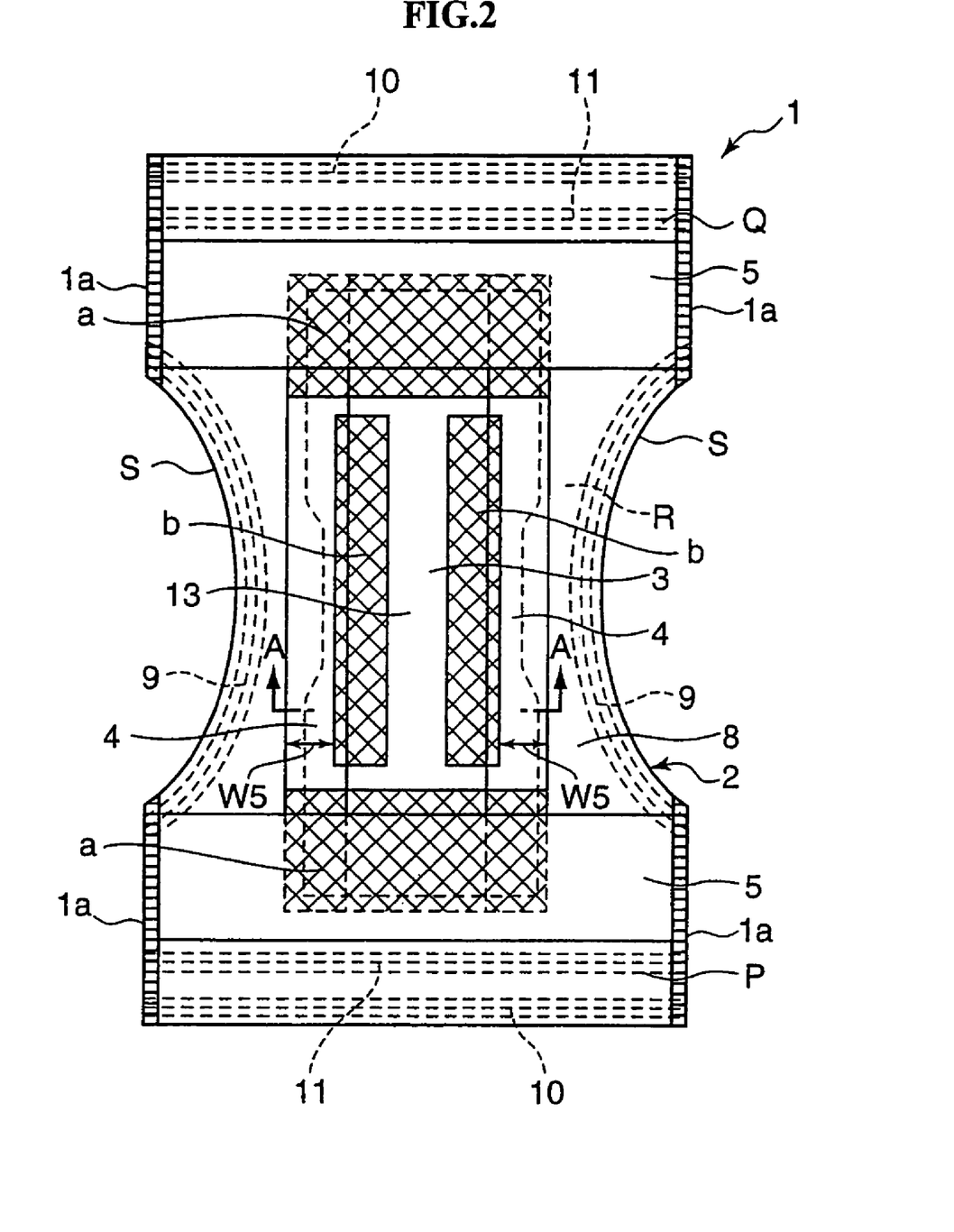
FIG. 2 is a plan view showing the disposable diaper of the pants type in a developed state.

Specifically, as shown in FIG. 2, the back sheet 14 in the absorbent main body 3 is attached by joining (see cross hatches "a") the entire front and rear ends of the back sheet 14 in the width direction onto the skin-contacting surface side of the second external sheet 8 and by joining (see cross hatches "b") a part of an intermediate portion between the front and rear ends in the width direction onto the skin-contacting surface side of the second external sheet 8 at an outermost joint position inward by a prescribed width W5 from the most side edge 3a of the absorbent main body 3. The entire intermediate portion may be joined in the width direction.

The prescribed width W5 may preferably be in the range of 10 mm to 40 mm, and most preferably, 15 m to 30 m. If the prescribed width W5 is smaller than 10 mm, the folded rising degree of each of both side ends 3b of the absorbent main body 3, described later, becomes undesirably small (see a solid line and an arrow "c" in FIG. 5(b)). In contrast, if the prescribed width W5 is greater than 40 mm, the shape stability of the absorbent main body 3 becomes undesirably deteriorated.

Although not specifically shown, in the front and back waist guards 5, guarding elastic yarns are joined in the width direction in an elongated state, and further, both ends and outer ends thereof are bonded onto the skin-contacting surface side of the second external sheet 8 of the external sheet 2 while inner ends are formed as free ends in such a manner that the front and back waist guards 5 cover the front and rear ends of the absorbent main body 3, respectively. As a result, the inner ends will naturally rise in the shape of a pocket inlet opening.

Each of the rising gathered members 4 and the waist guards 5 may preferably be made of a water repellent sheet, for which only a non-woven fabric or a laminated sheet composed of a non-woven fabric and a synthetic resin film may be used. Examples of the non-woven fabric include span-bond non-woven fabrics, span-bond/melt-blown/span-bond non-woven fabrics (i.e., SMS's), span-bond/melt-blown/melt-blown/span-bond non-woven fabrics (i.e., SMMS's), heat roll non-woven fabrics, air through non-woven fabrics, and the like. Examples of the film include films made of a thermoplastic resin such as polyethylene or polypropylene.

In addition, each of the rising gathered members 4 and the waist guards 5 may be made of a synthetic fiber non-woven fabric, at least inner surface of which has been subjected to water repellent or waterproof treatment. The outer surface thereof may preferably be made of a hydrophilic fiber which has not been subjected to water repellent or waterproof treatment from the viewpoint of pleasant touch, but it may also be made of a hydrophobic fiber.

Figure 3:
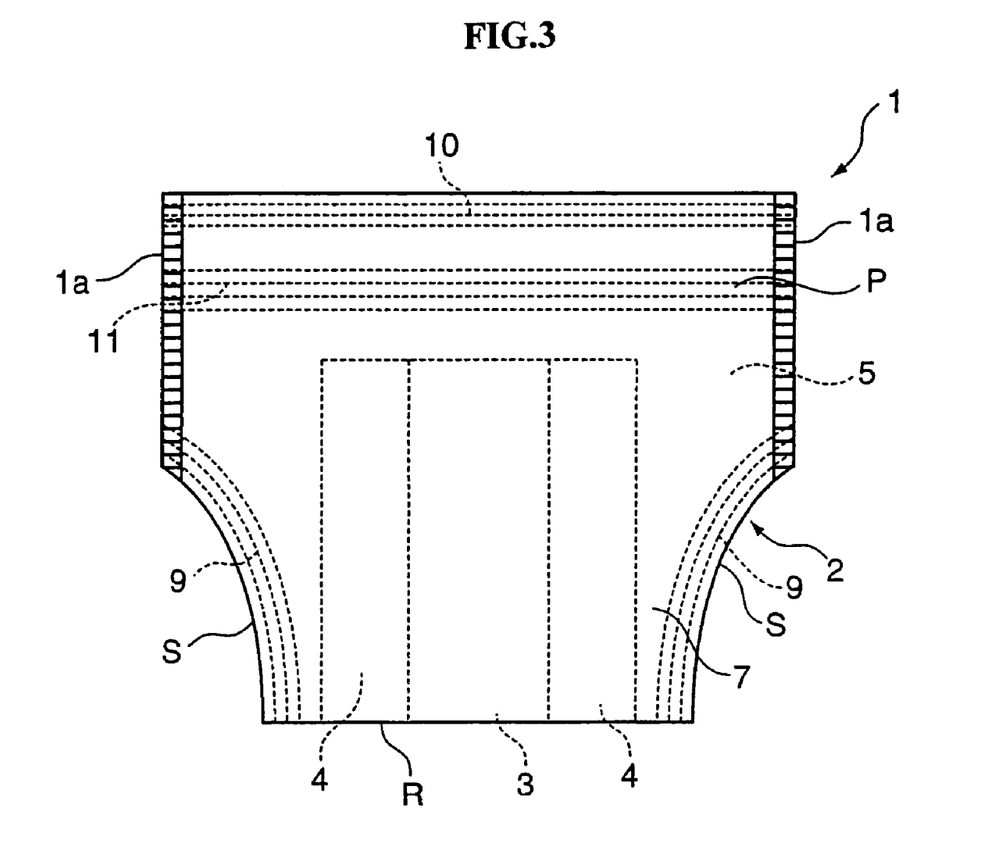
FIG. 3 is a front view showing the disposable diaper of the pants type in a completed state.

The external sheet 2 having the absorbent main body 3 with the rising gathers attached thereto is folded lengthwise in two at the boundary of the crotch part R, and then, the disposable diaper 1 of a pants type is assembled in a completed state by joining both side ends 1a of the front section P and the back section Q to each other, respectively, as shown in FIG. 3. A waist opening is formed at the upper portions of the front section P and the back section Q, and further, the leg openings S are formed on both sides of the crotch part R between the front section P and the back section Q.

In the disposable diaper 1 of the pants type, formed as described above, the inward folded base ends 4b are joined (see the marks x) astride both side ends 13a of the top sheet 13 serving as the top surface of the absorbent main body 3 and both side ends 14a of the back sheet 14 in such a manner that the rising gathered members 4 of the absorbent main body 3 attached to the external sheet 2 will rise from the most side edges 3a in the width direction of the absorbent main body 3, and therefore, the entire width W1 of the absorbent main body 3 becomes substantially equal to a rising width W6, thereby remarkably increasing an effective contact area with the skin, and further, thereby increasing a spatial width W7 between the rising gathered members 4, which thus hardly fall down on the absorbent main body 3, so as to remarkably increase an effective contact area with the skin.

Thus, even if the disposable diaper 1 of the pants type is shifted, it is possible to effectively prevent any lateral leakage of urine and the like.

As described above, with an increased spatial width W7 between the rising gathered members 4, in the case where replaceable urine pads are used in an overlap on the absorbent main body 3, the urine pad is readily placed between the rising gathered members 4 without any need of deformation of the rising gathered member 4 at the time of placement or any need of restriction of the rising gathered member 4 in a falling and lying state. Thus, even if the urine pad is used in an overlap on the absorbent main body 3, it is possible to effectively prevent any lateral leakage of urine and the like.

Moreover, the base end 4b of the rising gathered member 4 is merely joined astride the side end 13a of the top sheet 13 serving as the top surface of the absorbent main body 3 and the side end 14a of the back sheet 14, thereby requiring no top sheet winding step or the like in the conventional process. Therefore, such a simple process can achieve inexpensive production, and further, the stability of product precision becomes improved.

Figure 5:
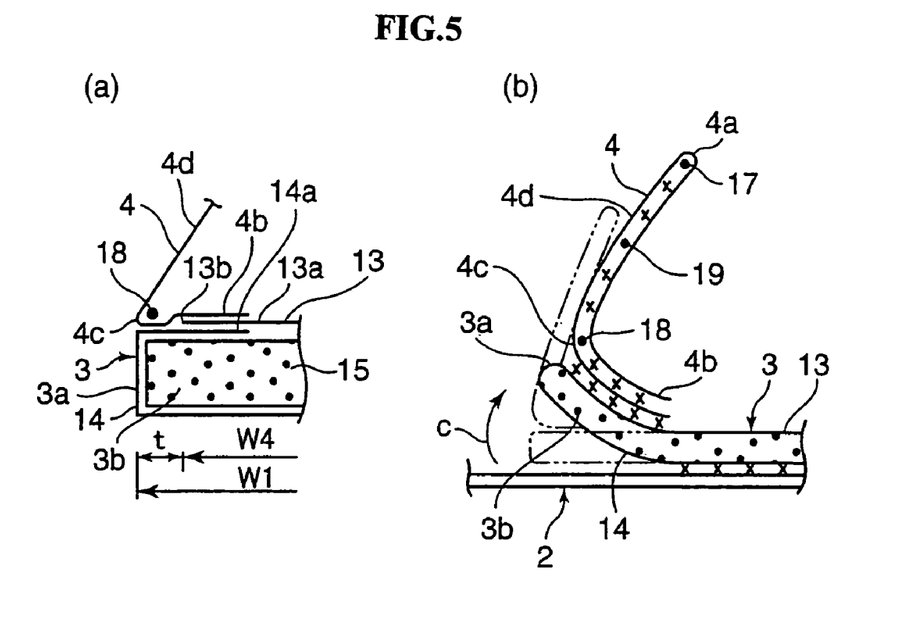
FIGS. 5(a) and 5(b) are schematically enlarged cross-sectional views showing a rising gathered portion.

In addition, the back sheet 14 of the absorbent main body 3 is attached at a position inward from the most side edge 3a of the absorbent main body 3 at an inward width W5 as an outermost joint position by joining the back sheet 14 onto the skin-contacting surface side of the second external sheet 8. Therefore, as shown in FIG. 5(b), when the rising gathered member 4 rises by the contractive force of the first gathering elastic yarn 17 and the like, the side end 3b of the absorbent main body 3 outside of the joint position also rises in a folded manner together with the rising gathered member 4 by the contractive force (see the arrow "c"), so that a high wall for preventing any leakage is formed together with the rising gathered member 4, thereby improving the property of fitting to the skin, so as to more effectively prevent any lateral leakage of urine and the like.

In addition, the front and rear ends of the back sheet 14 of the absorbent main body 3 are attached by joining (see the cross hatches "a" in FIG. 2) the entire surfaces onto the skin-contacting surface side of the second external sheet 8 in the width direction, thereby improving an attachment strength of the absorbent main body 3 with respect to the external sheet 2.

Furthermore, since the second gathering elastic yarn 18 extending lengthwise is joined to the rising base 4c of the rising gathered member 4 in an elongated state, the fold-like rising property of the side end 3b of the absorbent main body 3 becomes excellent together with the rising gathered member 4 in association with the first gathering elastic yarn 17 at the free end 4a, thereby improving the property of fitting to the skin, so as to effectively prevent any lateral leakage of urine and the like. When the third gathering elastic yarn 19 is joined to the rising portion 4d between the second gathering elastic yarn 18 and the first gathering elastic yarn 17 in an elongated state, the fold-like rising property of the side end 3b of the absorbent main body 3 becomes more excellent together with the rising gathered member 4 by the mutual interaction of the elastic yarns 17 to 19.

Moreover, the side end 13a of the top sheet 13, formed in a width smaller than that of the right end 14a, is joined to the side end 14a of the back sheet 14 of the absorbent main body 3, and the base end 4b of the rising gathered member 4 is joined astride the respective side ends 13a and 14a of the top and back sheets 13 and 14 so as to seal the end edge 13b of the side end 13a of the top sheet 13, thereby effectively preventing any leakage of urine and the like, which had been soaked into the top sheet 13, from the end edge 13b of the side end 13a.

In the above embodiment, the side end 14a of the back sheet 14 of the absorbent main body 3 is folded inward at the upper surface of the absorbent material 15, and then, the top sheet 13 is joined astride the upper surface of the absorbent material 15 and the upper surfaces of the side ends 14a of the back sheet 14, and further, the base end 4b of the rising gathered member 4 is joined astride the side ends 13a of the top sheet 13 and the side ends 14a of the back sheet 14. As a result, the end edge 13b of the side end 13a of the top sheet 13 is sealed at the base end 4b of each of the rising gathered members 4.

Figure 6:
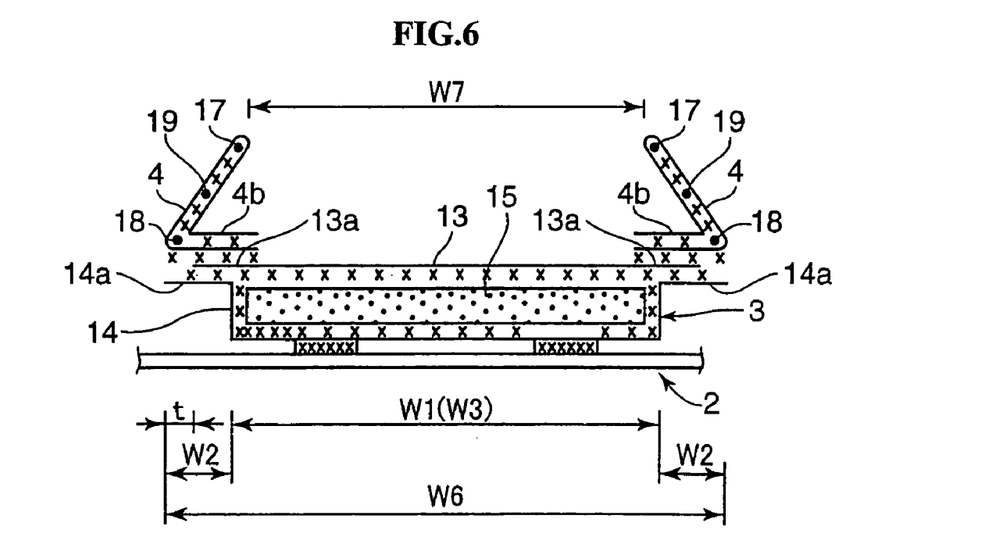
FIG. 6 is a schematically enlarged cross-sectional view taken along the line A-A of FIG. 2 in a modification of the disposable diaper of the pants type.

In contrast, the side end 14a of the back sheet 14 of the absorbent main body 3 may be folded outward, and further, the top sheet 13 having a width greater than the entire width W1 of the absorbent main body 3 may be joined astride the upper surface of the absorbent material 15 and the upper surfaces of the side ends 14a of the back sheet 14, as shown in FIG. 6. The clearance "t" may be formed between the side end 14a of the back sheet 14 and the side end 13a of the top sheet 13, and further, the base end 4b of the rising gathered member 4 may be joined astride the side ends 13a of the top sheet 13 and the side ends 14 of the back sheet 14. Consequently, the end edge 13b of the side end 13a of the top sheet 13 may also be sealed at the base end 4b of the rising gathered member 4.

In this manner, the rising width W6 between the rising gathered members 4 is increased to be a width obtained by adding a width W2 of the base end 4b to the entire width W1 of the absorbent main body 3, so that even if the disposable diaper 1 of the pants type is shifted, it is possible to effectively prevent any lateral leakage of urine and the like. Alternatively, a wide replaceable urine pad may also be used. Furthermore, an absorption effective width W3 of the absorbent main body 3 becomes substantially equal to the entire width W1, thereby improving the absorption performance of the absorbent main body 3.

Although each of the above embodiments is a disposable diaper 1 of the pants type having the absorbent main body 3 attached to the external sheet 2, the absorbent main body 3 can be attached alone to an existing diaper cover or the like with a tape, and then, can be used. Otherwise, the disposable diaper 1 of the pants type can be used as a replaceable urine pad in an overlap on an absorbent main body in an existing disposable diaper of the pants type. In addition, there may also be added constituent members well-known to those skilled in the art.

INDUSTRIAL APPLICABILITY

As can be seen from the above description, in the constitution as set forth in claim 1 according to the present invention, the inward folded base ends are joined to the side ends of the top surface of the absorbent main body in such a manner that the rising gathered members rise from the most side edges in the width direction of the absorbent main body. Consequently, the entire width of the absorbent main body becomes substantially equal to the rising width, thereby remarkably increasing an effective contact area with the skin. Furthermore, since the rising width between the rising gathered members becomes greater, the rising gathered members hardly fall down on the absorbent main body, thereby remarkably increasing an effective contact area with the skin.

Thus, in the case where the disposable absorbent article is used as it is, or it is used in attachment to an existing diaper cover or the like, it is possible to effectively prevent any lateral leakage of urine and the like, even if the disposable absorbent article is shifted. The base ends of the rising gathered members are merely joined to the side ends of the top surface of the absorbent main body, thereby requiring no sheet winding step or the like, so that such a simple process can achieve inexpensive production, and further, the stability of product precision becomes improved.

In the constitution as set forth in claim 2 according to the present invention, in the case where the absorbent main body is attached to the external sheet of the pants type, the inward folded base ends are joined to the side ends of the top surface of the absorbent main body in such a manner that the rising gathered members rise from the most side edges in the width direction of the absorbent main body. Consequently, the entire width of the absorbent main body becomes substantially equal to the rising width, thereby remarkably increasing an effective contact area with the skin. Furthermore, since the rising width between the rising gathered members becomes greater, the rising gathered members hardly fall down on the absorbent main body, thereby remarkably increasing an effective contact area with the skin.

Thus, it is possible to effectively prevent any lateral leakage of urine and the like, even if the external sheet of the pants type (i.e., the diaper) is shifted. In this manner, with an increased rising width (i.e., an effective width) between the rising gathered members, in the case where the replaceable urine pads are used in an overlap on the absorbent main body, the urine pad is readily placed between the rising gathered members without any need of deformation of the rising gathered member at the time of placement or any need of restriction in a falling and lying state. Thus, even if the urine pad is used in an overlap on the absorbent main body, it is possible to effectively prevent any lateral leakage of urine and the like.

In addition, the base ends of the rising gathered members are merely joined to the side ends of the top surface of the absorbent main body, thereby requiring no sheet winding step or the like, so that such a simple process can achieve inexpensive production, and further, the stability of product precision becomes improved.

Like the constitution as set forth in claim 3, the back sheet of the absorbent main body is attached by joining the back sheet onto the skin-contacting surface side of the crotch part of the external sheet at a position inward with a prescribed width from each of the most side edges of the absorbent main body as an outermost joint position. Thus, when the rising gathered member rises by the contractive force of the elastic member, both side ends of the absorbent main body outside of the joint position also raise in the folded manner together with the rising gathered member by the contractive force, so that the high wall for preventing any leakage is formed together with the rising gathered member, thereby improving the property of fitting to the skin, so as to effectively prevent any lateral leakage of urine and the like.

Like the constitution as set froth in claim 4, the front and rear ends of the back sheet of the absorbent main body are attached by entirely joining onto the skin-contacting surface side of the external sheet. Thus, it is possible to improve an attachment strength of the absorbent main body with respect to the external sheet.

Like the constitution as set forth in claim 5, the lengthwise extending elastic member is joined to at least either one of the rising base and the rising portion in the rising gathered member in an elongated state. Thus, the fold-like rising property of the side ends of the absorbent main body becomes excellent together with the rising gathered member in association with the elastic member at the free end, thereby improving the property of fitting to the skin, so as to effectively prevent any lateral leakage of urine and the like.

Like the constitution as set forth in claim 6, both side ends of the top sheet, formed in a width smaller than that of both right ends of the back sheet in the absorbent main body, are joined to the side ends of the back sheet, and further, the base end of the rising gathered member is joined astride the respective side ends of the top sheet and the back sheet so as to seal the end edges at both side ends of the top sheet. Thus, it is possible to effectively prevent any leakage of urine and the like, which has been soaked into the top sheet, from the end edges at both side ends.

The invention claimed is:

1. A disposable absorbent article, comprising:
an absorbent main body in which an absorbent material is interposed between a liquid-permeable top sheet and a liquid-impermeable back sheet;
rising gathered members disposed at both side ends of a top surface of the absorbent main body, each of the rising gathered members including a free end, a base end and a rising portion therebetween; and
a lengthwise extending elastic member joined to the free end in an elongated state, wherein
the base end is folded inward in a width direction of the absorbent main body, and is joined to each of the both side ends of the top surface in such a manner that the rising portion originates from an outermost side edge in a width direction of the absorbent main body and rises up therefrom.

2. A disposable absorbent article according to claim 1, further comprising:
an external sheet of a pants type having a waist opening formed at upper portions of a front section and a back section, and leg openings on both sides of a crotch part between the front section and the back section, wherein
the back sheet of the absorbent main body is attached to a skin-contacting surface side of the external sheet.

3. The disposable absorbent article according to claim 2, wherein the back sheet of the absorbent main body is attached to a skin-contacting surface side of a crotch part of the external sheet at a position inward with a prescribed width from each said outermost side edge of the absorbent main body as an outermost joint position.

4. The disposable absorbent article according to claim 2, wherein front and rear ends of the back sheet of the absorbent main body are attached entirely to the skin-contacting surface side of the external sheet.

5. The disposable absorbent article according to claim 1, wherein a lengthwise extending elastic member is joined to a base of the rising portion in the rising gathered member in an elongated state.

6. The disposable absorbent article according to claim 1, wherein both side ends of the top sheet, formed in a width smaller than that of both side ends of the back sheet in the absorbent main body, are joined to the side ends of the back sheet, and further, the base end of the rising gathered member is joined astride the side end of each of the top sheet and the back sheet so as to seal end edges at both side ends of the top sheet.

7. The disposable absorbent article according to claim 2, wherein a lengthwise extending elastic member is joined to a base of the rising portion in the rising gathered member in an elongated state.

8. The disposable absorbent article according to claim 2, wherein both side ends of the top sheet, formed in a width smaller than that of both side ends of the back sheet in the absorbent main body, are joined to the side ends of the back sheet, and further, the base end of the rising gathered member is joined astride the side end of each of the top sheet and the back sheet so as to seal end edges at both side ends of the top sheet.

9. The disposable absorbent article according to claim 1, wherein
the back sheet covers the lower and side surfaces of the absorbent material and both side ends of the back sheet are folded inward at the upper surface of the absorbent material; and
the width of the top sheet is smaller than an entire width of the absorbent main body.

10. The disposable absorbent article according to claim 2, wherein:
the back sheet covers the lower and side surfaces of the absorbent material and both side ends of the back sheet are folded inward at the upper surface of the absorbent material; and
the width of the top sheet is smaller than an entire width of the absorbent main body.

11. The disposable absorbent article according to claim 1, wherein the base end is joined to each of the both side ends of the top surface in such a manner the rising portion is integral with the outermost side edge in a width direction of the absorbent main body and rises up therefrom.

12. The disposable absorbent article according to claim 2, wherein the base end is joined to each of the both side ends of the top surface in such a manner the rising portion is integral with the outermost side edge in a width direction of the absorbent main body and rises up therefrom.

13. The disposable absorbent article according to claim 1, wherein the base end includes a fold at the outermost side edge and another portion extending inward in the width direction of the absorbent main body.

14. The disposable absorbent article according to claim 2, wherein the base end includes a fold at the outermost side edge and another portion extending inward in the width direction of the absorbent main body.

* * * * *